United States Patent
Kang et al.

(10) Patent No.: US 10,255,669 B2
(45) Date of Patent: Apr. 9, 2019

(54) DEFECT MEASURING DEVICE FOR WAFERS

(71) Applicant: LG SILTRON INC., Gumi-si, Gyeongsangbuk-do (KR)

(72) Inventors: Chi-Hun Kang, Gumi-si (KR); Kee-Yun Han, Gumi-si (KR)

(73) Assignee: SK Siltron Co., Ltd. (KR)

( * ) Notice: Subject to any disclaimer, the term of this patent is extended or adjusted under 35 U.S.C. 154(b) by 261 days.

(21) Appl. No.: 15/328,852

(22) PCT Filed: Jul. 28, 2015

(86) PCT No.: PCT/KR2015/007882
§ 371 (c)(1),
(2) Date: Jan. 24, 2017

(87) PCT Pub. No.: WO2016/018049
PCT Pub. Date: Feb. 4, 2016

(65) Prior Publication Data
US 2017/0213333 A1 Jul. 27, 2017

(30) Foreign Application Priority Data
Jul. 29, 2014 (KR) .................. 10-2014-0096449

(51) Int. Cl.
*H04N 9/47* (2006.01)
*G06T 7/00* (2017.01)
(Continued)

(52) U.S. Cl.
CPC .......... *G06T 7/0004* (2013.01); *G01N 21/94* (2013.01); *G01N 21/9501* (2013.01);
(Continued)

(58) Field of Classification Search
CPC ............ G01N 21/9501; G01N 21/9503; H01L 21/67288; H01L 22/12; H04N 7/181; G06T 2207/30148
See application file for complete search history.

(56) References Cited

U.S. PATENT DOCUMENTS

| | | | |
|---|---|---|---|
| 2003/0169916 | A1 | 9/2003 | Hayashi et al. |
| 2004/0197433 | A1 | 10/2004 | Terada et al. |

(Continued)

FOREIGN PATENT DOCUMENTS

| | | |
|---|---|---|
| CN | 1572015 A | 1/2005 |
| CN | 101276756 A | 10/2008 |

(Continued)

OTHER PUBLICATIONS

KIPO Notice of Allowance dated Jun. 24, 2015, issued in priority KR Application No. 10-2014-0096449, 2 pages.

(Continued)

*Primary Examiner* — Sathyanaraya V Perungavoor
*Assistant Examiner* — Peet Dhillon
(74) *Attorney, Agent, or Firm* — Lewis Roca Rothgerber Christie LLP (57) ABSTRACT

Provided is a device for measuring wafer defects, which prevents damage of a wafer and also measures defects at upper, lower and side surfaces of the wafer simultaneously. The device for measuring wafer defects includes a lower blower configured to inject air to a lower surface of a wafer to float the wafer; an upper blower provided to be moved up and down with respect to the lower blower and configured to inject the air to an upper surface of the wafer to fix the wafer; an upper contamination measuring part provided at an upper side of the upper blower and configured to detect contamination on the upper surface of the wafer; a lower contamination measuring part provided at a lower side of the (Continued)

lower blower and configured to detect contamination on the lower surface of the wafer; and a side contamination measuring part provided between the upper and lower blowers and configured to detect contamination on a side surface of the wafer.

11 Claims, 6 Drawing Sheets

(51) Int. Cl.
    *G01N 21/94*     (2006.01)
    *G01N 21/95*     (2006.01)
    *H04N 7/18*     (2006.01)
    *H01L 21/67*     (2006.01)
    *H01L 21/66*     (2006.01)

(52) U.S. Cl.
    CPC ... *G01N 21/9503* (2013.01); *H01L 21/67288* (2013.01); *H04N 7/181* (2013.01); *G06T 2207/30148* (2013.01); *H01L 22/12* (2013.01)

(56) References Cited

U.S. PATENT DOCUMENTS

| | | | |
|---|---|---|---|
| 2008/0094603 A1 | 4/2008 | Lee | |
| 2008/0225281 A1* | 9/2008 | Komuro | G01N 21/9503 356/237.2 |
| 2008/0239301 A1 | 10/2008 | Yokota et al. | |
| 2009/0181546 A1 | 7/2009 | Katoh et al. | |
| 2012/0132412 A1 | 5/2012 | Yamamoto et al. | |

FOREIGN PATENT DOCUMENTS

| | | |
|---|---|---|
| CN | 101276770 A | 10/2008 |
| CN | 103192463 A | 7/2013 |
| JP | 09326430 A * | 12/1997 |
| JP | H09-326430 | 12/1997 |
| JP | 2003-243465 A | 8/2003 |
| JP | 2006-017685 A | 1/2006 |
| KR | 2003-0069836 | 8/2003 |
| KR | 10-2004-0012404 | 2/2004 |
| KR | 10-2005-0006720 A | 1/2005 |
| KR | 10-0745371 | 8/2007 |
| KR | 2008-0071004 A | 8/2008 |
| KR | 10-2009-0032755 | 4/2009 |
| KR | 10-2010-0042340 | 4/2010 |
| KR | 10-2012-0012857 | 2/2012 |

OTHER PUBLICATIONS

International Search Report, corresponding to PCT/KR2015/007882, dated Nov. 26, 2015, 2 pages.

SIPO Office Action dated Aug. 28, 2018 for corresponding CN Application No. 201580041304.5 (5 pages).

* cited by examiner

DEFECT MEASURING DEVICE FOR WAFERS

CROSS-REFERENCE TO RELATED APPLICATION(S)

This application is a National Phase Patent Application and claims priority to and the benefit of International Application Number PCT/KR2015/007882, filed on Jul. 28, 2015, which claims priority to Korean Patent Application Number 10-2014-0096449, filed on Jul. 29, 2014, the entire contents of all of which are incorporated herein by reference.

FIELD

The present invention relates to a device for measuring wafer defects, which prevents contamination due to a contact of a wafer and also measures defects at upper, lower and side surfaces of the wafer.

BACKGROUND

Generally, a wafer goes through multiple processing processes, and in an operation of each of the processes, defects such as contamination, cracks and scratches may be generated.

Since the defects generated on a surface of the wafer may have a bad influence such as defect generation in a device process and reduction in yield, various wafer inspections are performed during a wafer manufacturing process.

In a related art, wafer defects were inspected visually. However, since the visual inspection has lower reliability and wafer defects may be additionally generated, the wafer defects are automatically inspected by a separate device.

In Korean Patent Publication No. 2010-0042340, there is disclosed a device for inspecting a rear surface of a semiconductor wafer, in which a center portion thereof is opened and a ring-shaped stage for supporting an edge surface of the rear surface of the semiconductor wafer is included.

In Korean Patent Publication No. 2004-0012404, there is disclosed a wafer support used in a device for inspecting a backside of a wafer, including a stage pin which protrudes on a wafer stage to support an edge portion of a wafer.

However, in such a device for measuring wafer defects according to the prior art, since a side surface or a lower surface of the wafer is supported, contamination may occur at the side surface or the lower surface of the wafer, and a measurement error may be generated in a process of inspecting the wafer defects.

SUMMARY

The present invention is directed to a device for measuring wafer defects, which is able to reduce contamination due to a contact of a wafer.

Also, the present invention is directed to a device for measuring wafer defects, which is able to simultaneously measure the defects at upper, lower and side surfaces of a wafer.

According to an aspect of the present invention, there is provided a device for measuring wafer defects, including a lower blower configured to inject air to a lower surface of a wafer to float the wafer; an upper blower provided to be moved up and down with respect to the lower blower and configured to inject the air to an upper surface of the wafer to fix the wafer; an upper contamination measuring part provided at an upper side of the upper blower and configured to detect contamination on the upper surface of the wafer; a lower contamination measuring part provided at a lower side of the lower blower and configured to detect contamination on the lower surface of the wafer; and a side contamination measuring part provided between the upper and lower blowers and configured to detect contamination on a side surface of the wafer.

The details of one or more embodiments are set forth in the accompanying drawings and the description below. Other features will be apparent from the description and drawings, and from the claims.

BRIEF DESCRIPTION OF THE DRAWINGS

Embodiments will be described in detail with reference to the following drawings in which like reference numerals refer to like elements, and wherein.

DETAILED DESCRIPTION

Hereinafter, embodiments will be described in detail with reference to the accompanying drawings. The scope of the invention may be determined by the disclosure of the embodiments, and the concept of the embodiments includes modification such as adding, removing and altering of elements.

Figure 1:
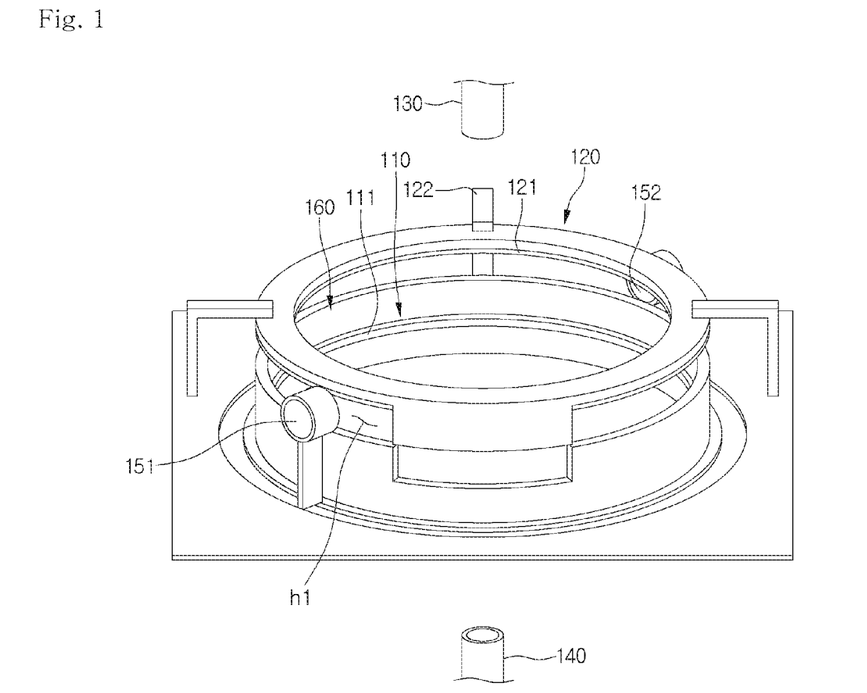
FIG. 1 is a perspective view of a device for measuring wafer defects according to an embodiment of the present invention.
Figure 2:
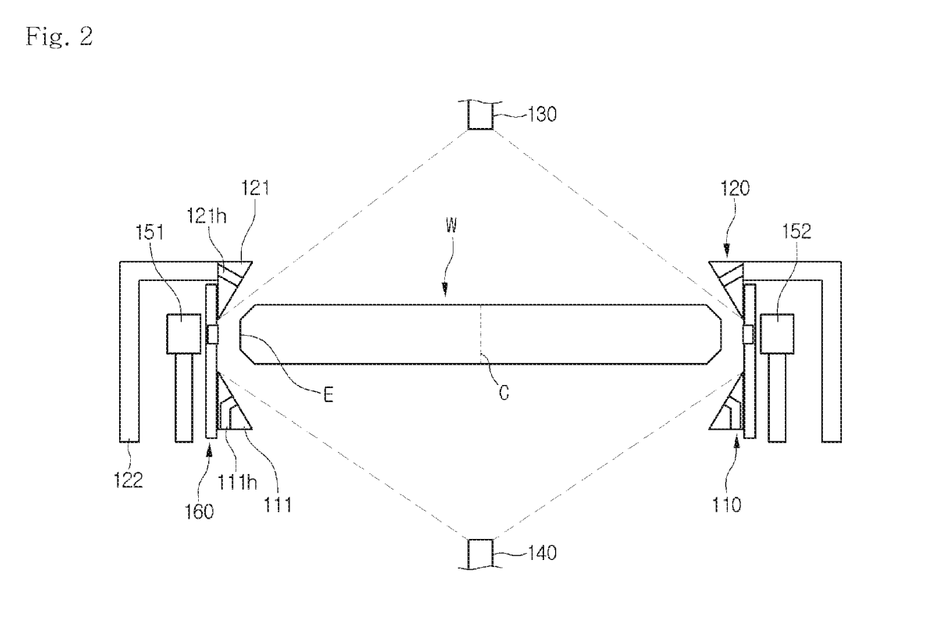
FIG. 2 is a side view illustrating the device for measuring wafer defects according to the embodiment of the present invention.
Figure 3:
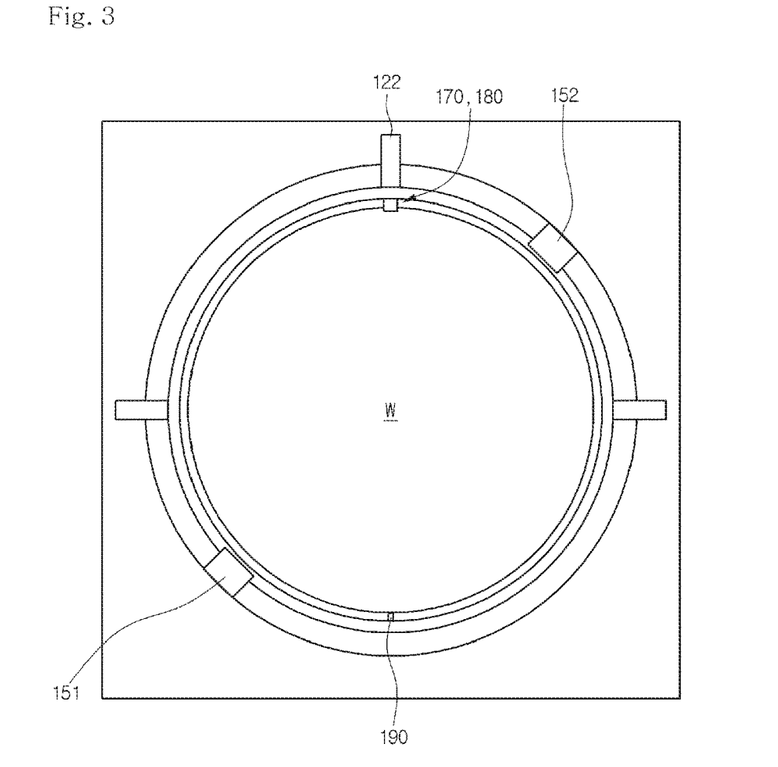
FIG. 3 is a plan view illustrating the device for measuring wafer defects according to the embodiment of the present invention.

FIGS. 1 to 3 are perspective views illustrating a device for measuring wafer defects according to an embodiment of the present invention.

As illustrated in FIGS. 1 to 3, a device for measuring wafer defects according to an embodiment of the present invention includes upper and lower blowers 110 and 120 for injecting air onto upper and lower surfaces of a wafer W, upper and lower contamination measuring parts 130 and 140 and side contamination measuring parts 151 and 152 for detecting contamination at upper, lower and side surfaces of the wafer W, an up and down movement guide part 160 for guiding an up and down movement of the wafer W, a notch measuring camera 170 for detecting a notch of the wafer W, a notch gripper 180 for gripping the notch of the wafer W, and a stopper 190 for radially supporting a portion of the wafer W opposite to the notch.

The lower blower 110 serves to float the wafer W by injecting air to a lower surface of the wafer W.

In the embodiment, the lower blower 110 may include a lower path 111 formed in a ring shape larger than a diameter of the wafer W and lower nozzles 111h provided to be spaced apart from each other at regular intervals in a circumferential direction of the lower path 111, and the lower path 111 is formed in a fixed state.

At this point, the lower blower 110 is configured to inject the air to a halfway point, i.e., a ½ point between a center C of the wafer W and an edge E thereof, thereby stably supporting the lower surface of the wafer W.

For example, an inner circumferential surface of the lower path 111 may be formed to be inclined, or an angle of each of the lower nozzles 111h may be formed to be inclined. However, the present invention is not limited thereto.

The upper blower 120 is provided to fix the floating wafer W by injecting the air to an upper surface of the wafer W.

In the embodiment, the upper blower 120 may include an upper path 121 formed in the ring shape larger than the diameter of the wafer W, a supply path 122 for supplying the air into the upper path 121 and upper nozzles 121h provided to be spaced apart from each other at regular intervals in a circumferential direction of the upper path 121, and the upper path 121 is formed to be movable up and down.

At this point, like the lower blower 110, the upper blower 120 is also configured to inject the air to the halfway point, i.e., the ½ point between the center C of the wafer W and the edge E thereof, thereby stably supporting the upper surface of the wafer W.

For example, an inner circumferential surface of the upper path 121 may be formed to be inclined, or an angle of each of the upper nozzles 121h may be formed to be inclined. However, the present invention is not limited thereto.

In the upper/lower blowers 110 and 120 as described above, an air pressure is controlled to horizontally float and fix the wafer W, and such a configuration will be described below in detail.

The upper contamination measuring part 130 is formed in a camera type which may take an image of the entire upper surface of the wafer W and provided at an upper side of the upper blower 120 to be movable, and the lower contamination measuring part 140 is formed in a camera type which may take an image of the entire lower surface of the wafer W and provided at a lower side of the lower blower 110 to be movable.

In the embodiment, an area CCD or an area CMOS camera may be used as each of the upper and lower contamination measuring parts 130 and 140, but the present invention is not limited thereto.

The side contamination measuring parts 151 and 152 are two cameras which may take an image of a side surface of the wafer W. The side contamination measuring parts 151 and 152 are provided to be movable in a circumferential direction of the wafer W.

In the embodiment, a CCD line scan camera may be used as each of the side contamination measuring parts 151 and 152, but the present invention is not limited thereto.

The up and down movement guide part 160 is formed in a cylindrical shape larger than the diameter of the wafer W so that the wafer W is accommodated therein and provided to prevent the wafer W from deviating from a predetermined range even when the wafer W is floated by an injection of the air.

At this point, the side contamination measuring parts 151 and 152 are provided outside the up and down movement guide part 160, and a separate measuring space h1 formed in a circumferential direction of the up and down movement guide part 160 is provided so that the side surface of the wafer W is measured by the side contamination measuring parts 151 and 152.

The notch measuring camera 170 and the notch gripper 180 are provided in a direction opposite to a direction of the stopper 190. The notch gripper 180 and the stopper 190 are configured to be in contact with a minimum area of the side surface of the wafer W in directions opposite to each other, and such a configuration will be described below in detail.

Figure 4:
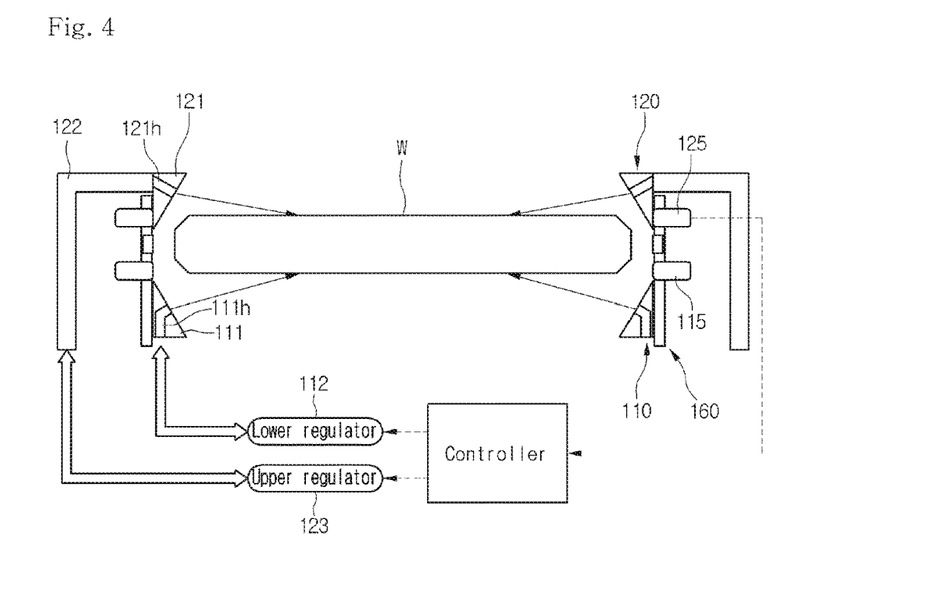
FIG. 4 is a view illustrating a structure of controlling an air injection pressure applied to the device for measuring wafer defects according to the embodiment of the present invention.
Figure 5:
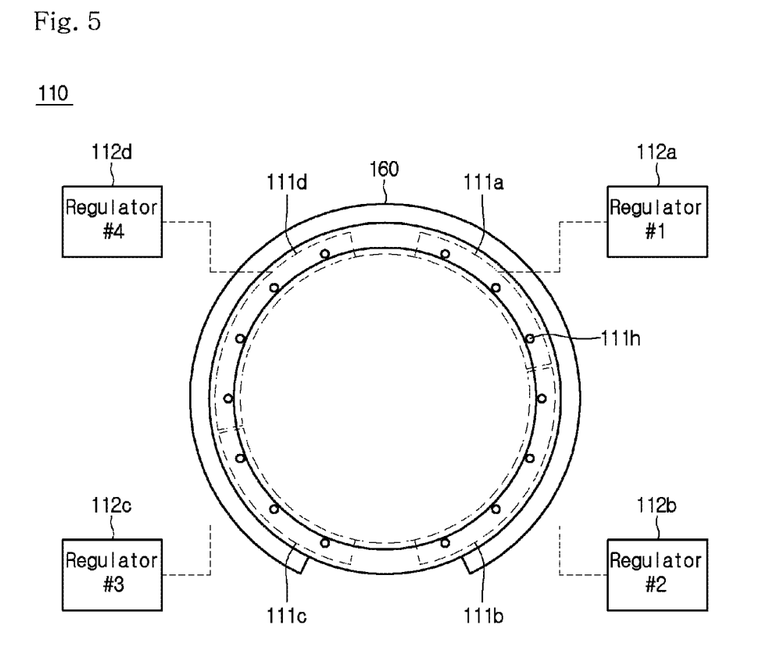
FIG. 5 is a view illustrating an example of a lower blower structure applied to FIG. 4.
Figure 6:
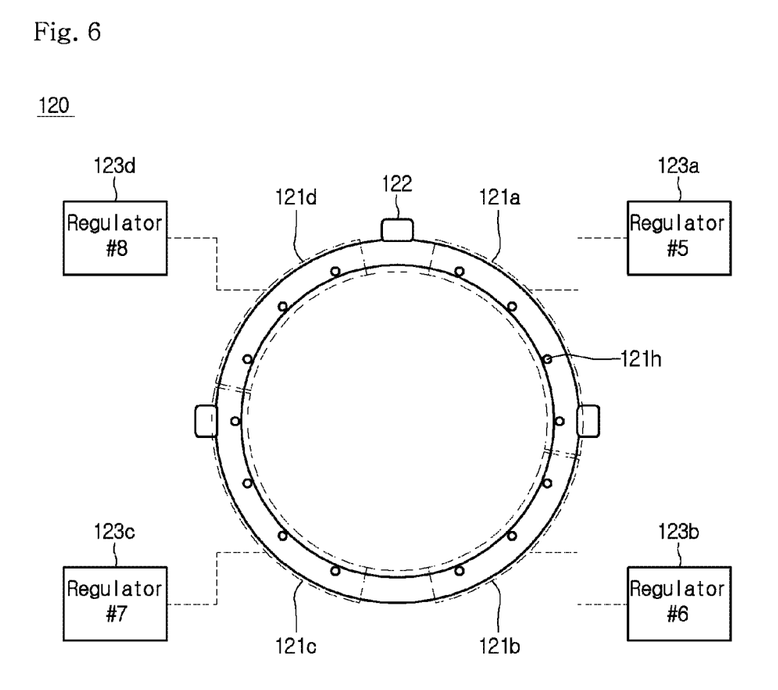
FIG. 6 is a view illustrating an example of an upper blower structure applied to FIG. 4.

FIGS. 4 to 6 are views illustrating an example of the upper/lower blowers for controlling an air injection pressure applied to the device for measuring wafer defects according to the embodiment of the present invention.

As illustrated in FIG. 4, the upper/lower blowers 110 and 120 further includes upper/lower regulators 112 and 123 for controlling the injection pressure of the air supplied to the upper/lower paths 111 and 121, a controller for controlling an operation of each of the upper/lower regulators 112 and 123, and upper/lower limit sensors 115 and 125 for detecting and transmitting positions of the upper/lower surfaces of the wafer to the controller.

Therefore, when an up and down movement position of the wafer is detected by the upper/lower limit sensors 115 and 125, the controller may control the injection pressure of the air supplied to the upper/lower paths 111 and 121 by controlling an operation of each of the upper/lower regulators 112 and 123 in consideration of the up and down movement position of the wafer, thus may float and fix the wafer to the above-described position in parallel with the side contamination measuring parts 151 and 152 and may also prevent the wafer from horizontally deviating even when the wafer is moved vertically by the up and down movement guide part 160.

However, since a diameter of each of the upper/lower paths 111 and 121 is increased as a diameter of the wafer is recently increased, such as 300 mm and 450 mm, the air pressure injected through the upper/lower nozzles 111h and 121h may be lowered as a distance from a portion of each of the upper/lower paths 111 and 121 to which the air is injected is increased, and thus the wafer may be inclined.

To compensate the problem, the upper/lower blowers 110 and 120 may be configured so that the upper/lower paths 111 and 121 are formed in a plurality of path units which are partitioned in a circumferential direction, and the upper/lower regulators 112 and 123 may be configured to separately control the injection pressure of the air supplied to each of the path units.

More specifically, as illustrated in FIG. 5, the lower blower 110 may include a plurality of lower path units 111a, 111b, 111c and 111d which are partitioned in the circumferential direction and a plurality of lower regulators 112a, 112b, 112c and 112d which control the injection pressure of the air supplied into each of the lower path units 111a, 111b, 111c and 111d.

In the embodiment, four lower path units 111a, 111b, 111c and 111d may be provided, and each of the lower path units 111a, 111b, 111c and 111d may be partitioned to have 3 to 4 nozzles 111h, and the air may be injected with the same air pressure from each of the nozzles 111h included in each of the lower path units 111a, 111b, 111c and 111d.

Also, as illustrated in FIG. 6, like the lower blower 110, the upper blower 120 may also include a plurality of upper path units 121a, 121b, 121c and 121d and a plurality of upper regulators 123a, 123b, 123c and 123d.

In the embodiment, four upper path units 121a, 121b, 121c and 121d may be provided, and each of the upper path units 121a, 121b, 121c and 121d may be partitioned to have 3 to 4 nozzles 121h.

A process in which the above-described upper/lower blowers 110 and 120 control the inclined wafer to become horizontal is as follows.

When the controller controls the air pressure of each of the upper/lower regulators 112a to 112d and 123a to 123d in consideration of an inclined direction and an inclined degree of the wafer detected by the above-described upper/lower limit sensors 115 and 125 (in FIG. 4), each of the upper/lower regulators 112a to 112d and 123a to 123d controls the air pressure supplied to each of the upper/lower path units 111a to 111d and 121a to 121d to be different from each other, and thus the wafer may be floated and fixed to a horizontal position by the air injected from each of the upper/lower nozzles 111h and 121h.

For example, when a certain point of the wafer is inclined downward based on the position in parallel with the side contamination measuring parts 151 and 152, the air pressure supplied to the lower path unit located at the certain point of the wafer may be controlled to be increased, or the air pressure supplied to the upper path unit located at the certain point of the wafer may be controlled to be reduced.

Figure 7:
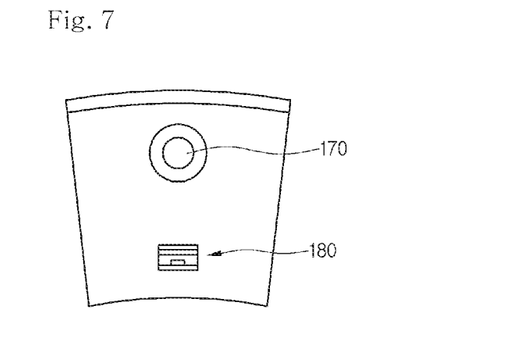
FIG. 7 is a view illustrating a structure of supporting a wafer notch applied to the device for measuring wafer defects according to the embodiment of the present invention.
Figure 8:
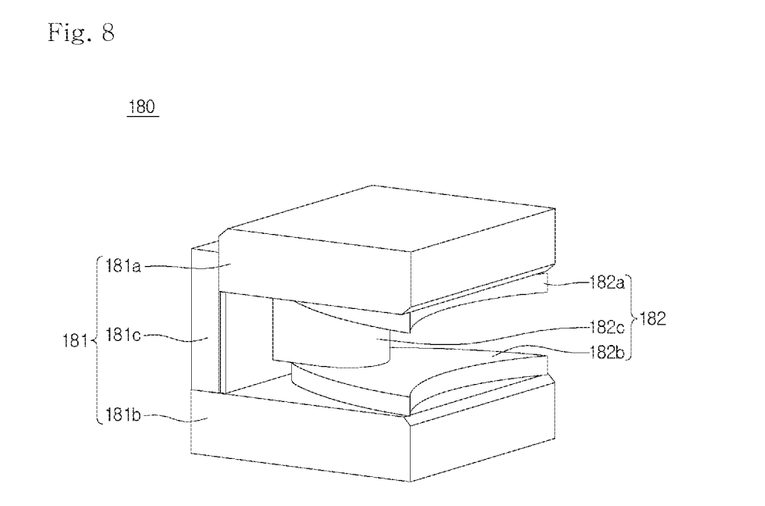
FIG. 8 is a view illustrating an example of a notch gripper structure applied to FIG. 7.
Figure 9:
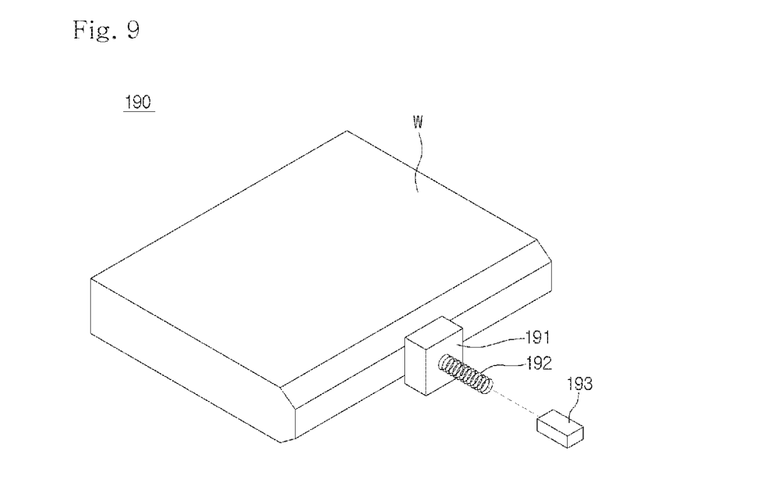
FIG. 9 is a view illustrating a stopper applied to the device for measuring wafer defects according to the embodiment of the present invention.

FIGS. 7 to 9 are views illustrating an example of a structure of supporting a side surface of the wafer applied to the device for measuring wafer defects according to the embodiment of the present invention.

To more stably support the wafer when the wafer is loaded between the above-described upper/lower blowers 110 and 120, it is configured to support a notch provided at the side surface of the wafer and an opposite side thereto. To this end, the notch measuring camera 170, the notch gripper 180 and the stopper 190 are provided.

As illustrated in FIG. 7, the notch measuring camera 170 and the notch gripper 180 are provided at upper/lower sides of an inner circumferential surface of the above-described up and down movement guide part 160.

The notch measuring camera 170 measures the notch of the wafer loaded by a robot arm, and then the robot arm is operated in consideration of a measured notch position of the wafer so that the notch of the wafer is engaged with the notch gripper 180.

As illustrated in FIG. 8, the notch gripper 180 is configured to be in contact with a minimum area of the notch N of the wafer and includes a cover part 181 and a buffer part 182 formed of a buffer material.

The cover part 181 has a '⊏'-shaped side surface, includes an upper surface portion 181a, a lower surface portion 181b and a side surface portion 181c and is formed in a shape which may accommodate the buffer part 182.

The buffer part 182 is provided inside the cover part 181, formed of the buffer material to absorb a shock even when being in direct contact with the wafer and includes an upper surface portion 182a, a lower surface portion 182b and a side surface portion 182c, like the cover part 181.

At this point, each of the upper/lower surface portions 182a and 182b may be formed in a flat plate shape, and the side surface portion 182c may be formed in a convexly rounded shape to minimize an area which is in direct contact with the side surface of the wafer.

As illustrated in FIG. 9, the stopper 190 is formed to be in contact with the minimum area of the notch of the wafer W and the opposite side thereto and includes a contact part 191, a spring part 192 and an air pressure controller 193.

The contact part 191 is a member which is in direct contact with the opposite side of the notch of the wafer W, may be supported by the spring part 192 and the air pressure controller 193 to be shock-absorbable in a radial direction of the wafer W and may be formed to support the wafer W having various diameters.

FIGS. 10A to 10D are views illustrating an operation example of the device for measuring wafer defects according to the embodiment of the present invention.

Figure 10A:
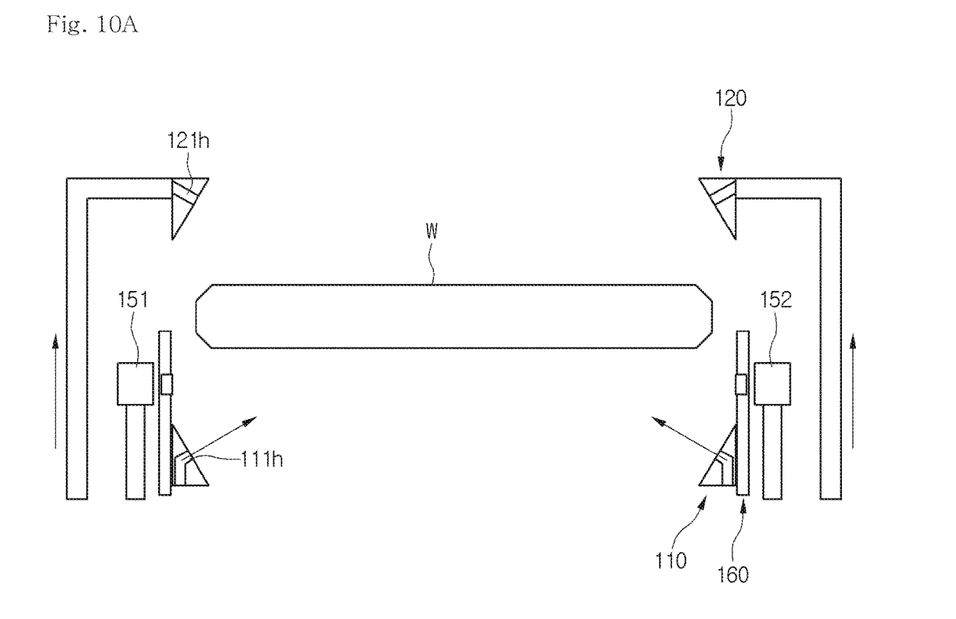
FIGS. 10A to 10D are views illustrating an operation example of the device for measuring wafer defects according to the embodiment of the present invention.

As illustrated in FIG. 10A, the lower blower 110 is moved upward, and the wafer W is loaded between the upper/lower blowers 110 and 120 by the robot arm.

Figure 10B:
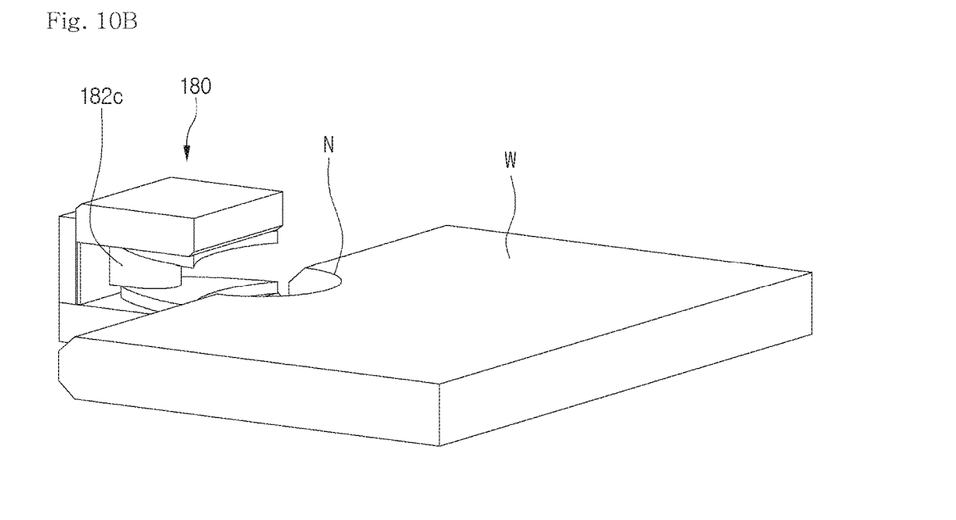

As illustrated in FIG. 10B, when the notch N of the wafer W is measured by the notch measuring camera 170, the robot arm moves down the wafer W so that the notch N of the wafer W is gripped by the notch gripper 180 and the opposite side of the wafer W is buffered and supported by the stopper 190.

At this point, since the side surface portion 182c of the notch gripper 180 which is in contact with the side surface of the notch N of the wafer W is formed to be rounded, the contamination of the wafer W due to a contact may be minimized, and thus the wafer W may be more stably supported.

Figure 10C:
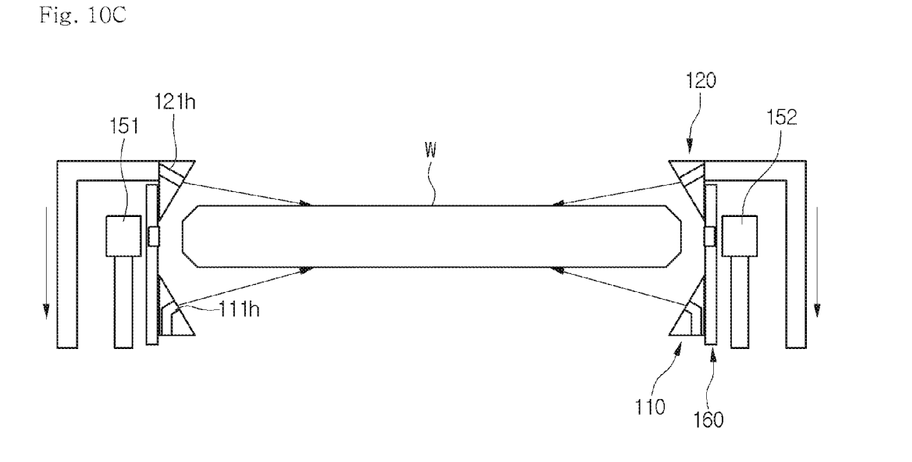

As illustrated in FIG. 10C, when the air is injected to the lower surface of the wafer W through the lower nozzle 111h of the lower blower 110, the wafer W is floated and guided by the up and down movement guide part 160 to be prevented from deviating.

At this point, since the lower nozzles 111h inject the air to the halfway point between the center of the lower surface of the wafer W and the edge thereof, the wafer W may stably float.

Of course, the robot arm is separated from the wafer W and then goes out while the wafer W is supported by the notch gripper 180 and the stopper 190 and is floated by the lower blower 110.

Also, when the air is injected to the upper surface of the wafer W through the upper nozzle 121h while the upper blower 120 is moved down, the wafer W is fixed in a floated state due to the air pressure injected from the upper/lower blowers 110 and 120.

At this point, the wafer W is floated and fixed at the position in parallel with the side contamination measuring parts 151 and 152. As described above, the air pressure injected from the upper/lower nozzles 111h and 121h may be controlled according to a signal detected by the upper/lower limit sensors 115 and 125, and detailed description thereof will be omitted.

Figure 10D:
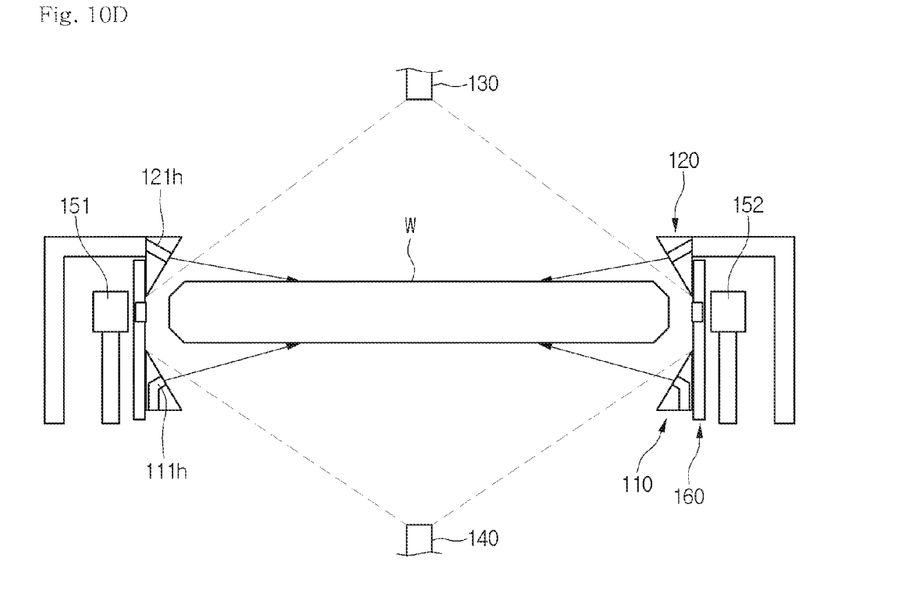

As illustrated in FIG. 10D, the upper/lower contamination measuring parts 130 and 140 are located at upper/lower sides of the wafer W and then measure defects on the upper/lower surfaces of the wafer W, and the side contamination measuring parts 151 and 152 measure the defects on the side surface of the wafer W while moving in the circumferential direction.

As described above, the upper/lower contamination measuring parts 130 and 140 and the side contamination measuring parts 151 and 152 may simultaneously measure the defects on the upper, lower and side surfaces of the wafer W.

Since the device for measuring wafer defects according to the present invention has the upper/lower blowers for injecting the air to the upper and lower surfaces of the wafer and thus can measure the wafer detects while the wafer is floated and fixed, it is possible to prevent a contact with the upper/lower surfaces of the wafer, thereby preventing the contamination of the wafer and also to reduce a defect rate of the wafer.

Also, since the device for measuring wafer defects according to the present invention has the upper contamination measuring part, the lower contamination measuring part and the side contamination measuring part for detecting the contamination of the wafer without interference with the upper/lower blowers and thus can simultaneously measure the defects on the upper, lower and side surfaces of the wafer while the wafer is floated and fixed, the defects on the entire wafer can be rapidly detected, and thus productivity of the wafer can be increased.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A device for measuring wafer defects, comprising:
    a lower blower configured to inject air to a lower surface of a wafer to float the wafer;
    an upper blower provided to be moved up and down with respect to the lower blower and configured to inject the air to an upper surface of the wafer to fix the wafer;
    an upper contamination measuring part provided at an upper side of the upper blower and configured to detect contamination on the upper surface of the wafer;
    a lower contamination measuring part provided at a lower side of the lower blower and configured to detect contamination on the lower surface of the wafer; and
    a side contamination measuring part provided between the upper and lower blowers and configured to detect contamination on a side surface of the wafer.

2. The device according to claim 1, wherein each of the upper and lower blowers includes a ring-shaped path through which the air flows and a plurality of nozzles which are arranged at the path at regular intervals and through which the air is injected to the upper and lower surfaces of the wafer.

3. The device according to claim 2, wherein each of the upper and lower blowers has an air injection angle of 45° at which the air is injected to the upper and lower surfaces of the wafer and injects the air to a halfway point between a center of the wafer and an edge thereof.

4. The device according to claim 2, wherein the path is partitioned into a plurality of path units so that the nozzles are divided into at least two or more groups, and each of the path units is connected to a regulator to adjust an injection pressure of the air.

5. The device according to claim 4, wherein each of the upper and lower blowers further includes a limit sensor to detect an inclination of each of the upper and lower surfaces of the wafer, and the regulator adjusts the injection pressure of the air supplied into the path units according to the inclination detected by the limit sensor.

6. The device according to claim 1, wherein the side contamination measuring parts are at least two or more cameras which are movable in a circumferential direction of the wafer.

7. The device according to claim 1, further comprising an up and down movement guide part provided between the upper and lower blowers and configured to guide an up and down movement of the wafer.

8. The device according to claim 1, further comprising a notch measuring camera configured to measure a notch of the wafer;
    a notch gripper configured to grip the notch of the wafer measured by the notch measuring camera; and
    a stopper provided in a direction opposite to that of the notch gripper and configured to radially support a side of the wafer opposite to the notch.

9. The device according to claim 8, wherein a portion of the notch gripper which is in contact with a part of upper, lower and side surfaces of the notch of the wafer is formed of a buffer material.

10. The device according to claim 8, wherein the notch gripper includes a rounded side surface portion to reduce a contact area with a part of a side surface of the notch of the wafer.

11. The device according to claim 8, wherein the stopper is pneumatically controlled to radially buffer and support the wafer.

* * * * *